United States Patent [19]
Igarashi et al.

[11] Patent Number: 4,610,927
[45] Date of Patent: * Sep. 9, 1986

[54] MICROCAPSULES CONTAINING A HYDROPHOBIC, VOLATILE CORE SUBSTANCE AND THEIR PRODUCTION

[75] Inventors: Yuriko Igarashi, Iwaki; Masaaki Takahashi, Tokyo, both of Japan

[73] Assignee: Kureha Kagaku Kogyo Kabushiki Kaisha, Tokyo, Japan

[ * ] Notice: The portion of the term of this patent subsequent to Jul. 17, 2001 has been disclaimed.

[21] Appl. No.: 647,636

[22] Filed: Sep. 6, 1984

[30] Foreign Application Priority Data

Sep. 14, 1983 [JP] Japan ................................. 58-169789
Sep. 19, 1983 [JP] Japan ................................. 58-172739

[51] Int. Cl.$^4$ ........................ B01J 13/02; B32B 27/00
[52] U.S. Cl. ........................... 428/402.21; 71/DIG. 1; 252/522 A; 264/4.7; 424/19; 424/32; 525/936
[58] Field of Search ...................... 264/4.7; 428/402.21; 424/19, 32; 71/DIG. 1; 525/936; 252/522 A

[56] References Cited

U.S. PATENT DOCUMENTS 3,607,775  9/1971  Yoshida et al. .................. 264/4.7 X
3,981,821  9/1976  Kiritani et al. .................. 264/4.7 X
4,353,809 10/1982  Hoshi et al. ........................ 264/4.7
4,460,722  7/1984  Igarashi et al. ................. 264/4.7 X

FOREIGN PATENT DOCUMENTS 2178686 11/1973  France .
2305229 10/1976  France .
1230854  5/1971  United Kingdom .
2073697 10/1981  United Kingdom .
2109331  6/1983  United Kingdom .

Primary Examiner—Richard D. Lovering
Attorney, Agent, or Firm—Oblon, Fisher, Spivak, McClelland & Maier

[57] ABSTRACT

Disclosed herein are microcapsules containing a hydrophobic, volatile substance as the core substance, a wall membrane of the microcapsule comprising a polymer made by interfacial polymerization of a polyvalent isocyanate with a water-soluble cationic urea resin and/or a prepolymer of aminoresin, and a resin made by polycondensing the water-soluble cationic urea resin with the prepolymer of aminoresin in the presence of a low-molecular anionic surfactant, and a process for producing the microcapsules.

7 Claims, No Drawings

MICROCAPSULES CONTAINING A HYDROPHOBIC, VOLATILE CORE SUBSTANCE AND THEIR PRODUCTION

BACKGROUND OF THE INVENTION

1. Field of the Invention

The present invention relates to microcapsules containing a hydrophobic, volatile substance as a core substance and a process for producing the same.

2. Discussion of the Background

Microencapsulation of perfumes, agricultural chemicals, adhesive agents and the like which contain hydrophobic, volatile substance(s), for instance, a fraction boiling at a low temperature has been demanded from the viewpoints of preventing the volatilization of the volatile substance as an active ingredient during preservation of the perfumes, agricultural chemicals, component(s) of adhesive agent and the like.

Although there are various proposed methods for microcapsulating the hydrophobic, organic compounds hitherto (for instance, refer of Japanese Patent Publication No. 771/1967), since it is impossible in the conventional methods to form a wall membrane of the microcapsules, which is completely dense and compact, the maintenance of the core substance in the microcapsules is insufficient. Accordingly, in the case of subjecting a volatile substance to microencapsulation as the core substance, the loss of the volatile substance is large due to evaporation in the step of microcapsulation and the step of drying the wet microcapsules. As a result the reduction of the yield of microcapsulation is caused, and in addition, the evaporation of the volatile substance causes the formation of micro-pores in the wall membrane of the microcapsules, thereby inducing the large defect of remarkably reducing the heat-resistance and solvent-resistance of the thus obtained microcapsules.

A process for microcapsulation by interfacial polymerization of a polyvalent isocyanate with water or a polyvalent amine has been known(refer of Japanese Patent Publication No. 771/1967). However, since the wall membrane of the microcapsules, which is formed by interfacial polymerization is a single membrane consisting of polyurea and it is impossible to obtain the membrane provided with a sufficiently compact and dense structure, it is inevitable that the capability of the wall membrane in retaining a volatile substance as the core substance within the microcapsules is very poor. Accordingly, the process is poor in practicality for microcapsulating a volatile substance.

The present invention provides microcapsules from which the volatile substance as the core substance does not dissipate during the steps of microcapsulation and drying by microcapsulating the hydrophobic, volatile substance, particularly the organic compound with a completely compact and dense wall membrane. The other objects will become clear from the following description.

SUMMARY OF THE INVENTION

In a first aspect of the present invention, there is provided microcapsules containing a hydrophobic, volatile substance as the core substance, wherein a wall membrane of the microcapsule comprises a polymeric material formed by the interfacial polymerization of polyvalent isocyanate with a water-soluble cationic urea resin and/or a prepolymer of an aminoresin, and a polymeric material formed by polycondensation of the water-soluble cationic urea resin with the prepolymer of an aminoresin in the presence of a low-molecular anionic surfactant.

In a second aspect of the present invention, there is provided a process for producing microcapsules containing a hydrophobic, volatile substance as the core substance, comprising dispersing the hydrophobic, volatile substance containing polyvalent isocyanate in an aqueous medium containing a water-soluble cationic urea resin, a low-molecular anionic surfactant and at least one prepolymer of aminoresin, and maintaining the pH of the resulting dispersion within an acidic range by adding an acid catalyst to interfacially polymerize the polyvalent isocyanate with the water-soluble cationic urea resin and/or the at least one prepolymer and to precondense the water-soluble cationic urea resin with the at least one prepolymer.

DETAILED EXPLANATION OF THE INVENTION

The characteristic of the present invention lies in (1) that the microcapsules containing a hydrophobic, volatile substance as the core substance have a wall membrane comprising a polymeric material formed by interfacial polymerization of polyvalent isocyanate with a water-soluble cationic urea resin and/or a prepolymer of aminoresin and a resinous material formed by polycondensation of a water-soluble cationic urea resin with a prepolymer of aminoresin in the presence of a low-molecular anionic surfactant and (2) that the hydrophobic, volatile substance is microencapsulated by dispersing the hydrophobic, volatile substance containing the polyvalent isocyanate in an aqueous mixture containing one or more kinds of the prepolymer of aminoresin, the water-soluble cationic urea resin and the anionic surfactant, and maintaining the pH of the resulting dispersion within an acidic range.

Namely, the present invention has been based on the finding that the microcapsules provided with a wall membrane of a completely compact and dense structure are available by forming a composite wall membrane on the surface of the hydrophobic, volatile substance as the core substance, the composite wall membrane being obtained by reacting the polymer of polyvalent isocyanate, the water-soluble cationic urea resin and the prepolymer of aminoresin in an aqueous medium.

In order to form the above-mentioned composite wall membrane according to the present invention, (1) the hydrophobic, volatile substance which is used as the core substance and contains the polyvalent isocyanate is dispersed in an aqueous solution containing the prepolymer of aminoresin, the water-soluble cationic urea resin and the low-molecular anionic surfactant, (2) the prepolymer of aminoresin and the water-soluble cationic urea resin are polycondensed while causing complex-coacervation by the water-soluble cationic urea resin and the low-molecular anionic surfactant in the presence of an acid catalyst, thereby (3) the hydrophobic, high polymeric wall membrane which covers the above-mentioned hydrophobic, volatile substance dispersed as minute particles in the aqueous solution is formed to complete the microencapsulation.

In the above-mentioned process, the polyvalent isocyanate contained in the core substance reacts with water, the prepolymer of aminoresin or the water-soluble cationic urea resin to form the hydrophobic, high-polymeric membrane on the interface of the core substance, thereby serving the purpose of completing the covering of the core substance.

Since in the microencapuslation according to the present invention, the formation of the wall membrane is carried out while dispersing the core substance containing the polyvalent isocyanate in an aqueous medium in which the water-soluble cationic urea resin is coexistent with the oppositely charged low-molecular anionic surfactant and prepolymer of aminoresin, it is possible to form a wall membrane comprising the composite membrane of a completely compact and dense structure. Since the thus formed microcapsules comprising the wall membrane and the core substance covered therewith become to powdery capsules excellent in solvent-resistance and heat-resistance by drying the former, they are effectively applicable as the microcapsules containing a hydrophobic, volatile substance such as organic solvent, agricultural chemical, perfume and component(s) of adhesive agent as the core substance.

The hydrophobic, volatile substance as the core substance contained in the microcapsules according to the present invention is a substance showing a vapour pressure of higher than 30 mmHg at 100° C., and particularly, an organic compound provided with the above-mentioned properties. For instance, benzene, toluene, xylene, hexane, heptane, trichloroethylene, tetrachloroethylene, carbon tetrachloride and mixtures of two or more than two thereof, anisole, methyl benzoate, ethyl isovalerate, allyl isocyanate, ethyl caproate, tetrahydrolinalool, isoamyl propionate and mixtures of more than two thereof, perfumes extracted from natural substances and agricultural chemicals, for instance, di(-chloroisopropyl) ether and allethrin may be exemplified. In addition, any compound showing a vapour pressure of below 30 mmHg at 100° C. may be used as the core substance after being mixed with one of the above-mentioned substances.

In the adhesive agent, in order to obtain the highest adhesion in a short time period, a volatile organic solvent such as xylene, toluene, benzene, hexane, heptane and trichloroethylene is mainly used.

In the case of producing the microcapsules according to the present invention, the polyvalent isocyanate contained in the hydrophobic, volatile substance as the core substance is a compound having two or more than two isocyanate groups (-NCO), and as such an isocyanate, tolylene diisocyanate, diisocyanatodiphenylmethane, hexamethylene diisocyanate, polymethylene poly-phenyl isocyanate, triisocyanatotriphenylmethane, dimer of tolylene diisocyanate and trimer of tolylene diisocyanate may be exemplified. In addition, commerciallized substances such as Coronate®HL and Coronate®L (made by Nippon Urethane Co., Ltd.) and Desmodur®TT, L, N, R (made by Bayer Co.) can be used as an isocyanate.

The isocyanate is contained in an amount of 0.1 to 50 parts by weight per 100 parts by weight of the hydrophobic, volatile substance.

Also, the isocyanate is contained in the core substance at a rate of 1 to 100 parts by weight, preferably 5 to 50 parts by weight to 100 parts by weight of the aminoplast-prepolymer used for microcapsulation.

As the prepolymer of aminoresin for use in microcapsulation according to the present invention, prepolymers of urea-formaldehyde resin (hereinafter referred to as UF prepolymer), prepolymers of melamine-formaldehyde resin (hereinafter referred to as MF prepolymer), prepolymers of melamine-urea-formaldehyde resin (hereinafter referred to as MUF prepolymer), prepolymers of melamine-thiourea-formaldehyde resin (hereinafter referred to as MTUF prepolymer) and prepolymers of melamine-urea-thiourea-formaldehyde resin (hereinafter referred to as MUTUF prepolymer) may be exemplified.

The term "MF prepolymer" means mono-, di-, tri-, tetra-, penta- and hexa-methylolmelamine and mixtures thereof as well as mixtures of melamine, formaldehyde and the above-mentioned methylolmelamine(s), and in addition, an aqueous transparent colloidal solution containing oligomers, obtained by treating the methylolmelamine of a degree of polymerization of 2 to 10 with hydrochloric acid, thereby further advancing the reaction between melamine and formaldehyde may be used as MF prepolymer.

The term "UF prepolymer" means mono-, di-, tri- and tetramethylolurea and mixture thereof as well as mixtures of the above-mentioned methylolurea(s), urea and formaldehyde. In addition, an aqueous transparent colloidal solution of oligomers of a degree of polymerization of 2 to 5, provided with hydrophilic groups and obtained by advancing the reaction between urea and formaldehyde further may be used as UF prepolymer.

On the other hand, MUF prepolymer, MTUF prepolymer and MUTUF prepolymer which are respectively made by heating a mixture of formaldehyde with at least two selected from melamine, urea and thiourea in alkaline range, mixture of two or more than two thereof and mixture of more than one thereof with the MF prepolymer and/or UF prepolymer may be used.

It should be added that the ratio between the starting materials, i.e., melamine, urea and thiourea to formaldehyde gives an important influence on the formation of the wall membrane of the microcapsules. The preferable molar ratio of formaldehyde to melamine is 1.0 to 9.0, more preferably 1.6 to 7.0, the preferable molar ratio of formaldehyde to urea is 0.6 to 4.0, more preferably 0.8 to 3.0 and the preferable molar ratio of formaldehyde to thiourea is 0.6 to 4.0, more preferably 0.8 to 3.0. However, the ratio between melamine, urea and thiourea may be optionally selected. The above-mentioned respective ratios of formaldehyde to melamine, urea and thiourea are selected to control the formation of the wall membrane of the microcapsules for providing the wall membrane with the strength and the permeability suited for the purpose.

In the process of microencapsulation, the prepolymer of aminoresin is preferably used in an amount of 0.01 to 1.0 g as a resin per 1 g of the hydrophobic, volatile substance as the core substance.

The water-soluble cationic urea resin for use in capsulation according to the present invention is made by introducing a cationic modifier into a urea-formaldehyde resin, and for instance, it is easily obtainable by adding a modifier such as tetraethylenepentamine, diaminoethanol, dicyanodiamide, diethylaminoethanol, guanylurea or the like to UF prepolymer and subjecting the mixture to polycondensation following a known method. It is preferable to select the weight ratio of the water-soluble cationic urea resin to the aminoplast-prepolymer in the range of 1:0.01 to 2.0. In addition, as a commerciallized cationic urea resin, Uramin®-P 1500 (an aqueous 33% by weight solution, made by Mitsui-Toatsu Co., Ltd.) may be exemplified.

As the low-molecular anionic surfactant for use according to the present invention, salts of fatty acids, sulfuric esters of higher alcohols and salts of alkylarylsulfonic acids may be exemplified, and sodium dodecylbenzenesulfonate is preferable.

A stable aqueous dispersion of the reactants used according to the present invention is available in a broad range of pH of from 2.5 to 6.5 by using the above-mentioned anionic surfactant in an amount of 0.01 to 0.1 part by weight to 1 part by weight of the water-soluble cationic urea resin.

As the acid catalyst for accelerating the reaction for microcapsulation according to the present invention, a low-molecular carboxylic acid such as formic acid, an inorganic acid such as hydrochloric acid, nitric acid and phosphoric acid, an acidic salt or an easily hydrolyzable salt such as aluminum sulfate, titanium oxychloride, magnesium chloride, ammonium chloride, ammonium nitrate, ammonium sulfate and ammonium acetate may be exemplified. Such a catalyst is used singly or in combination thereof.

A process for microencapsulating the hydrophobic, volatile (organic) compound by using the polyvalent isocyanate, prepolymer of aminoresin, water-soluble cationic urea resin and low-molecular anionic surfactant will be explained as follows.

At first, the hydrophobic, volatile substance containing the polyvalent isocyanate is dispersed in an aqueous mixture in which at least one water-soluble cationic urea resin and one low-molecular anionic surfactant are present by a suitable emulsifying means, for instance, a homogenizer, a stirrer or ultrasonic wave in a minute emulsified state.

As the prepolymer of aminoresin may have been present preliminarily in the aqueous mixture, it may be added during or after emulsifying the reactants at once or at several times.

Microencapsulation is carried out thereafter by the addition of the acid catalyst to the thus obtained aqueous dispersion containing the prepolymer of aminoresin, thereby reacting the reactants at a temperature of 15 to 60° C. and a pH of 2.5 to 6.0 for 2 to 50 hours while gently stirring the aqueous dispersion containing the prepolymer of aminoresin. In addition, an appropriate amount of water may be added to the reaction system during the reaction.

The wall membrane of the microcapsules obtained by the process of microencapsulation is a composite membrane formed of the polymeric material made by the interfacial polymerization of the polyvalent isocyanate with the water-soluble cationic urea resin and/or the prepolymer of aminoresin and the resinous material made by polycondensation of the water-soluble cationic urea resin with the prepolymer of aminoresin in the presence of the low-molecular anionic surfactant, and since the composite membrane has a compact and dense structure, the hydrophobic, volatile substance contained within the microcapsules as the core substance is effectively retained within the microcapsule without being lost even in the step of drying the wet microcapsule recovered from the aqueous medium, and thus obtained microcapsules are excellent in solvent-resistance and heat-resistance.

Accordingly, when the present invention is applied to microcapsulation of a hydrophobic, volatile organic compound such as organic solvents, perfumes and agricultural chemicals, it is profitable from the view point of preventing the evaporation of the volatile organic compound in storage and safety in use thereof.

In addition, the application of microcapsules according to the present invention to the adhesive agent of chemical reaction type and also to the adhesive agent of solvent-reactivation type will be concretely explained.

Adhesive Agent of Chemical Reaction Type

In the case where the microcapsules according to the present invention is applied to the adhesive agent of chemical reaction type, which comprises a resin for adhesion, an initiator of the reaction and a hardening agent, it may be preferable to include any one of the above-mentioned components within the microcapsules and to disperse the thus formed microcapsules in the other component(s). The component selected to be included within the microcapsules is the initiator of the reaction or the hardening agent which are generally relatively smaller in the amount used. The number of the components included within the microcapsule may be two or more than two, and each of the components which are to be encapsulated is separately subjected to microencapsulation or two or more than two of the components may be capsulated together with. As the resin for adhesion, polymethacrylic acid, polyacrylic acid, epoxy resin, polyester, polyamide, polyurethane-polyacrylate, polyurethane-polymethacrylate, polyester-polyacrylate, polyester-polymethacrylate, polyvinyl acetate, polystyrene, epoxy-polyacrylate, epoxy-polymethacrylate, their monomers, low-molecular silicone resin, natural rubber and neoprene rubber may be exemplified. To the above-mentioned resin or a solution of the resin in an organic solvent, the microcapsules containing solution of the initiator for the reaction and the hardening agent in an organic solvent are dispersed in a necessary amount. As the initiator for the reaction, a solution of dibutyltin dilaurate or stannous caprylate in the organic solvent, or a solution of the organic peroxide such as benzyl peroxide, dibutyl peroxide and cumenyl peroxide in an organic solvent may be exemplified. As the hardening agent, a solution of N,N-dimethylaniline and N,N-dimethyltoluidine in an organic solvent may be exemplified.

Adhesive Agent of Solvent-Reactivation Type

In the case where the microcapsules according to the present invention is applied to the adhesive agent of solvent-reactivation type, it may be profitable to disperse the microcapsules containing as the core substance a solvent for activating the resin constructing the adhesive membrane in a resin constructing the adhesive membrane. As the organic solvent capable of being microencapsulated, almost every solvent used generally can be applied, and for instance, toluene, hexane, heptane, benzene, xylene, carbon tetrachloride, trichloroethylene and tetrachloroethylene may be exemplified. As the resin reactivated by such a solvent, neoprene rubber, butyl rubber, styrene-butadiene rubber, natural rubber, polystyrene, polyvinyl acetate, methylcellulose, ethylcellulose, polyvinyl chloride, copolymer of ethylene and vinyl acetate, acrylic resin, methacrylic resin, polyamide resin and copolymer of vinyl acetate and acrylate may be exemplified.

The adhesive agent of solvent-activation type is produced by dispersing a necessary amount of the above-mentioned microcapsules containing the solvent into the resin which is to form the adhesive membrane as has been stated above, and in case of using the adhesive agent, a solution of the resin component of the adhesive agent is painted on the surface of one of the object to be adhered together and at the time of necessitating the adhesion, the surface is pressed onto the surface of the other object, then the microcapsules are easily broken to release the content thereof, thus resulting in the firm adhesion of the two objects.

The microcapsules prepared according to the present invention are easily separated from the aqueous phase which has been used for preparing the microcapsules and dried to obtain in a free-flowable powdery state and accordingly, such microcapsules are remarkably suitable to be processed into the adhesive agent of microcapsule type because of the excellent solvent-resistance thereof.

In addition, by dispersing the thus obtained powdery microcapsules in a solution of the resin component which is to construct the adhesive membrane in an organic solvent, the thus prepared solution can be painted onto the surface of one of the objects to be adhered together for further treatment.

Furthermore, since the microcapsules according to the present invention can be easily broken by applying a pressure of less than several tens kilograms per $cm^2$, by pressing an object, on the surface of which the microcapsules have been painted, onto the other object, the adhesion between the two objects can be conveniently carried out and accordingly, the adhesive agent of microcapsule type has a merit of being applicable to a broad field of adhesion.

The present invention will be explained more in detail while referring to the following non-limitative examples.

EXAMPLE 1

Preparation of an Prepolymer of Aminoresin 63 g of melamine and 162 g of an aqueous 37% solution of formaldehyde adjusted to pH of 9.0 by an aqueous 2% solution of sodium hydroxide were mixed together and the mixture was reacted at 70° C. Just after finding of the dissolution of melamine, 225 g of water was added to the mixture and the resultant mixture was stirred for 3 min, thereby preparing an aqueous solution of a prepolymer of melamine-formaldehyde (hereinafter referred to as M4F prepolymer).

Separately, 146 g of an aqueous 37% solution of formaldehyde adjusted to pH of 8.5 by adding triethanolamine and 60 g of urea were mixed together and the mixture was reacted at 70° C. for one hour, thereby obtaining a prepolymer of urea-formaldehyde (hereinafter referred to as U 1.8 F prepolymer).

Preparation of a Water-Soluble Cationic Urea Resin

To a stirred mixture of 162 g of an aqueous 37% solution of formaldehyde and 60 g of urea, triethanolamine was added to adjust the pH of the mixture to 8.8, the mixture was reacted at 70° C. for 30 min. Into 40 g of the reaction mixture, 3 g of tetraethylenepentamine and 24 g of water were added, the mixture was reacted at 70° C. for one hour while stirring the mixture and adjusting the pH thereof to 3 by the addition of aqueous 15% solution of hydrochloric acid. The thus reduced pH of the reaction mixture was readjusted to 3 by the addition of aqueous 10% solution of sodium hydroxide, and the reaction mixture was cooled to 55° C. while continuing the reaction. At the time point when the viscosity of the reaction mixture became 200 cps, the reaction mixture was neutralized by the addition of aqueous 10% solution of sodium hydroxide and 400 g of water were added to the neutralizate, thereby obtaining an aqueous solution of a water-soluble cationic urea resin.

Microencapsulation

Xylene was used as the core substance.

A mixture of 100 g of M4F prepolymer, 50 g of U 1.8 F prepolymer, 144 g of the above-mentioned cationic urea resin, 65 g of water and 1 g of triethanolamine was adjusted to pH of 4.8 by the addition of an aqueous 10% solution of citric acid, and thereafter 30 g of an aqueous 6% solution of a sodium alkylbenzenesulfonate (Neoperex ®, made by Kao-Atlas Co., Ltd.) were added to the mixture. Into the thus prepared liquid, 100 g of xylene which contained 30 g of a polyvalent isocyanate (a commerciallized substance with the registered trade mark of Coronate L (made by Nippon Polyurethan Co., Ltd.)) were dispersed as minute particles of 5 to 20 micrometers in a mean diameter.

The thus obtained aqueous dispersion was reacted at a constant temperature of 30° C. by the addition of an aqueous 10% solution of citric acid to adjust the pH of the dispersion to 3.6 while gently stirring thereof for one hour. After one hour of reaction, 200 g of water were added to the reaction mixture, and after further one hour, the aqueous 10% solution of citric acid was added to the reaction mixture to adjust the pH of the reaction mixture to 3.0. Stirring was further carried out for 25 hours to complete microcapsulation of the core substance. After collecting and washing the thus formed microcapsules with water, they were dried in a hot-air drier at 35° C. to obtain powdery microcapsules of 5 to 20 micrometers in a mean diameter.

EXAMPLES 2 to 11

In the same procedures as in Example 1 except for using each of the polyvalent isocyanates and each of the prepolymers of aminoresin in the respective amounts as shown in Table 1, thereby controlling the diameter of the thus obtained microcapsules in a range shown in Table 1, microcapsulation was carried out, the preparation of the prepolymer of aminoresin used in Examples 2 to 11 being carried out as shown below.

TABLE 1

| No. of Example | Prepolymer of aminoresin | | Polyvalent isocyanate | | Diameter of microcapsule (micrometer) |
|---|---|---|---|---|---|
| | Kind | amount (g) | Kind | amount (g) | |
| 2 | U 1.8 F | 100 | Coronate L | 5 | 30 to 50 |
| 3 | M4F | 130 | Coronate L | 20 | 10 to 30 |
| 4 | M4F + TU 1.8 F | 70 + 20 | Coronate L | 100 | 2 to 8 |
| 5 | M6F + TU 1.8 F + U 1.8 F | 38 + 18 + 18 | Coronate HL | 30 | 5 to 20 |
| 6 | M6F + TU 1.8 F + U 1.8 F | 45 + 10 + 20 | Coronate HL | 40 | 10 to 30 |
| 7 | MTU4F | 170 | Triphenylmethylene triisocyanate | 30 | 10 to 30 |
| 8 | MTUU5F | 122 | Trimer of tolylene diisocyanate | 30 | 10 to 30 |
| 9 | MU4F | 200 | Dimer of tolylene | 5 | 5 to 20 |

TABLE 1-continued

| No. of Example | Prepolymer of aminoresin Kind | amount (g) | Polyvalent isocyanate Kind | amount (g) | Diameter of microcapsule (micrometer) |
|---|---|---|---|---|---|
| 10 | MU4F + TU 1.8 F | 100 + 35 | diisocyanate Hexamethylene diisocyanate | 1 | 30 to 70 |
| 11 | MTU4F + U 1.8 F | 80 + 50 | Diisocyanate-4,4'-diphenylmethane | 0.5 | 30 to 70 |

Preparation of TU 1.8 F prepolymer

A mixture of 146 g of aqueous 37% solution of formaldehyde adjusted to pH of 8.5 thereof by adding triethanolamine and 76 g of thiourea was reacted at 70° C. for one hour to obtain an aqueous solution of a prepolymer of thioureaformaldehyde resin (hereinafter referred to TU 1.8 F Prepolymer).

Preparation of MTU4F prepolymer

A mixture of 324 g of aqueous 37% solution of formaldehyde adjusted to pH of 9.0 thereof by adding aqueous 2% solution of sodium hydroxide, 63 g of melamine and 38 g of thiourea was reacted at 70° C., and just after finding the dissolution of melamine and thiourea, 425 g of water were added to the reaction mixture and the resultant solution of a prepolymer of melamine, thiourea and formaldehyde resin (hereinafter referred to as MTU4F prepolymer) was cooled as it is to room temperature.

Preparation of MTUU5F prepolymer

A mixture of 405 g of aqueous 37% solution of formaldehyde adjusted to pH of 8.5 thereof by adding triethanolamine, 42 g of melamine, 25 g of thiourea and 20 g of urea was reacted at 70° C. for one hour, and then the reaction mixture was cooled to room temperature to obtain an aqueous solution of a prepolymer of melamine, thiourea, urea and formaldehyde resin (hereinafter referred to as MTUU5F prepolymer).

Preparation of MU4F prepolymer

A mixture of 324 g of aqueous 37% solution of formaldehyde adjusted to pH of 8.5 thereof by adding triethanolamine, 63 g of melamine and 30 g of urea was reacted at 70° C. for 30 min, and 225 g of water were added to the reaction mixture to obtain an aqueous solution of a prepolymer of melamine, urea and formaldehyde resin (hereinafter referred to as MU4F prepolymer).

The yield of microcapsulation, the volatility and the solvent-resistance of the powdery microcapsules, respectively obtained in Examples 1 to 11 were examined by the following methods and the results thereof are shown in Table 2 which also shows the results on the powdery microcapsules prepared respectively in Comparative Examples 1 and 2.

Methods of Examination (1) The yield of microencapsulation
The yield of microencapsulation was obtained from the following formula:

$$\text{Yield of microencapsulation (\%)} = \frac{W_i}{W_0} \times 100$$

wherein $W_i$ is the total weight of the core substance in the powdery microcapsules and $W_0$ is the weight of the core substance used in microencapsulation, i being the number of Example.

(2) The volatility
The volatility of the powdery microcapsules is expressed by the rate of retaining the core substance, obtained from the following formula:

$$\text{Rate of remaining (\%)} = \frac{W_{ii}}{W_i} \times 100$$

wherein $W_{ii}$ is the total weight of the core substance remained in the powdery microcapsules after preserving for 5 hours in a hot-air drier at 100° C., $W_i$ is the same as above.

(3) The solvent-resistance of the powdery microcapsules was examined as follows.

After immersing 1 g of the specimen of the powdery microcapsules in 20 ml of acetone for 24 hours at 20° C., the amount of the core substance exudated into acetone is measured and the solvent-resistance is expressed by the percentage of the weight of the core substance exudated into acetone to the weight of the core substance remained in the thus treated powdery microcapsules.

(4) The amount of the core substance in the microcapsules is measured as follows:

An accurate amount (nearly 1 g) of the powdery microcapsules is crushed in a small ball mill of 100 ml in capacity for 30 min, and the thus crushed material is extracted with 20 ml of acetone. The content of the core substance in the acetone extract is determined by gas chromatography.

COMPARATIVE EXAMPLE 1

In the same procedures as in Example 1 except for using xylene not containing the polyvalent isocyanate (Coronate L), microcapsulation was carried out. In Comparative Example 1, the presence of not-capsulated xylene was observed in the steps of emulsification and polymerization, respectively.

COMPARATIVE EXAMPLE 2

In the same procedures as in Example 1 except for (1) using xylene not containing the polyvalent isocyanate (Coronate L) and (2) using 147 g of water instead of both 144 g of the aqueous solution of the cationic urea resin and 3 g of the aqueous 6% solution of Neoperex ® in Example 1, microcapsulation was carried out.

In Comparative Example 2, it was observed that a considerable amount of xylene (as the core substance) was not capsulated and remained outside the microcapsules while forming a so-called freeoil layer.

TABLE 2

| Number of example | Yield of microcapsulation (%) | Volatility (%) | Solvent-resistance (%) |
|---|---|---|---|

TABLE 2-continued

| | Yield of micro-capsulation (%) | Volatility (%) | Solvent-resistance (%) |
|---|---|---|---|
| 1 | 90 | 95 | |
| 2 | 90 | 78 | 85 |
| 3 | 99 | 88 | 91 |
| 4 | 100 | 93 | 99 |
| 5 | 100 | 94 | 99 |
| 6 | 99 | 93 | 96 |
| 7 | 92 | 92 | 96 |
| 8 | 99 | 90 | 95 |
| 9 | 95 | 78 | 86 |
| 10 | 88 | 75 | 87 |
| 11 | 80 | 70 | 85 |
| Comparative Example | | | |
| 1 | 53 | 38 | 20 |
| 2 | 0 | 0 | 0 |

As are seen in Table 2, the microcapsules according to the present invention and the process for producing the same are superior to those of Comparative Examples 1 and 2.

EXAMPLE 12

After preparing a mixture of 15.0 g of M4F prepolymer, 3 g of Uramin ®P-1500 (an aqueous 38% solution of a cationic urea resin, prepared by Mitsui-Toatsu Co., Ltd.), 30 g of water and 0.15 g of triethanolamine and adjusting the pH thereof to 5.7 by the addition of an aqueous 10% solution of citric acid, 0.45 g of an aqueous 10% solution of sodium dodecylbenzenesulfonate was added to the mixture to obtain "A" liquid.

Separately, into a mixed perfume prepared by mixing each 5 g of anisol, benzyl benzoate and ethyl isovalerate, 2 g of a polyvalent isocyanate (Coronate L) were dissolved to obtain "B" liquid.

In a homogenizer, "B" liquid was dispersed into "A" liquid to obtain an aqueous emulsion in which the mixed perfume was dispersed as minute particles of 2 to 15 micrometers in diameter. Thereafter, 7.5 g of U 1.8 F prepolymer were added to the aqueous emulsion while gently stirring and maintaining thereof at 30° C., and the pH of the thus obtained mixture was adjusted to 3.3 by adding aqueous 10% solution of citric acid. After leaving the mixture stand still for one hour, 45 ml of water were added, and after stirring the mixture for 5 hours, the mixture was heated to 50° C. and maintained at the temperature for 24 hours under stirring to complete the encapsulation.

In the thus obtained slurry of the microcapsules, any presence of not-capsulated perfume was not observed.

After separating the microcapsules from the thus obtained slurry by a membrane-filter and washing the separated microcapsules with water and the thus washed microcapsules were dried in a hot-air drier for 16 hours at 50° C. to obtain the powdery microcapsules.

After crushing 1 g of the thus obtained powdery microcapsules in a small ball mill of 100 ml in capacity for 30 min, the thus crushed material was subjected to extraction with 20 ml of acetone, and the gas chromatographic pattern of the thus extracted perfume (a mixture) was compared to that of the original mixed perfume. No substantial difference was observed between the two patterns. The separately measured yield of microencapsulation was 95%.

EXAMPLE 13

After adjusting the pH of a mixture of 3 g of Uramin ®P-1500 and 0.13 g of triethanolamine to 4.8 by adding aqueous 10% solution of formic acid, 0.45 g of aqueous 10% solution of sodium n-dodecylbenzenesulfonate was added to the mixture, and after further adding water to the mixture to make the whole volume of the mixture to 80 ml, 15 ml of isoamyl propionate containing 0.5 g of Coronate HL was added to the mixture, and it was subjected to homogenization to obtain an emulsion of the minute particles of isoamyl propionate of 8 to 10 micrometers in diameter. While gently stirring the dispersed system at 30° C., the pH of the system was adjusted to 3.5 by the addition of aqueous 10% solution of formic acid, and the system was stirred for 20 hours at 45° C. to complete microencapsulation.

After separating the thus obtained microcapsules from the slurry by a membrane-filter and washing the thus separated microcapsules two times with water, the thus washed microcapsules were dried in a hot-air drier at 40° C. for 24 hours to obtain the powdery microcapsules containing isoamyl propionate as the core substance.

A flexo-printing ink was prepared by uniformly dispersing 25 g of the thus obtained powdery microcapsules into a vehicle for inking of a mixed solvent of 37 g of isopropyl alcohol, 18 g of ethyl acetate, 18 g of butyl acetate and 2 g of ethyl cellosolve, the mixed solvent containing 15 g of ethylcellulose dissolved therein, the viscosity of the thus prepared flexo-printing ink being 80 cps at 25° C.

On printing the thus prepared ink onto a sheet of fine paper of 50 g/m$^2$ by a flexo-printer, a printed matter with an evenly printed surface was obtained at an amount of printing of 1.0 g (as isoamyl propionate)/m$^2$. When the printed surface of the thus obtained printed sheet of paper was rubbed, the sheet emitted a strong fragrance suggestive of that of pineapples.

EXAMPLE 14

After adjusting the pH of a mixture of 3 g of Uramin ®, 40 g of water and 0.10 g of triethanolamine to 5.2 by the addition of aqueous 6% solution of citric acid, 0.2 g of aqueous 6% solution of sodium n-dodecylbenzenesulfonate was added to the thus adjusted mixture, and after adding 18 ml of allethrin containing 1 g of a trimer of tolylene diisocyanate dissolved therein into the mixture, the mixture was subjected to homogenization to disperse the thus added allethrin as minute particles of 3 to 8 micrometers in diameter. While gently stirring the dispersed system at 30° C., the pH of the system was adjusted to 3.6 by the addition of aqueous 6% solution of citric acid, and after one hour of stirring, 45 ml of water were added to the system and the system was continuously stirred for 20 hours, thereby completing microencapsulation.

Into 10 g of the thus obtained slurry of the microcapsules, 25 ml of aqueous 10% solution of polyvinyl alcohol of a degree of saponification of 100% were added, and the thus obtained mixture was sprayed onto the internal sides of a wardrobe.

On examining the remaining amount of allethrin on the internal sides thereof, 80% by weight of the sprayed allethrin remained thereon, and it was found that the wardrobe was useful as a wardrobe protected by a slow-releasing insecticide.

EXAMPLE 15

Microencapsulation

A mixture of 100 g of M4F prepolymer prepared in Example 1, 50 g of U 1.8 F prepolymer prepared in Example 1, 158 g of the aqueous solution of the water-soluble cationic urea resin prepared in Example 1, 62 g of water and 1 g of triethanol amine was adjusted to pH of 5.2 by the addition of aqueous 10% solution of citric acid, and after further adding 3 g of an aqueous 10% solution of sodium alkylbenzenesulfonate (Neoperex ®, made by Kao-Atlas Co., Ltd.) to the thus treated mixture to obtain "A" liquid.

Into "A" liquid, 150 ml of xylene containing 60 g of Coronate L ® (a commerciallized polyvalent isocyanate, made by Nippon Polyurethane Co., Ltd.) were dispersed as minute droplets of 5 to 20 micrometers in diameter, and after heating the thus prepared aqueous dispersion to 30° C., it was adjusted to pH of 3.6 by the addition of aqueous 10% solution of citric acid and reacted for one hour while gently stirring thereof and maintaining thereof at 30° C. Thereafter, 200 g of water were added to the reaction mixture and after one hour, the pH thereof was readjusted to 3.0 by the addition of aqueous 10% solution of citric acid. By further stirring the reaction mixture continuously for 18 hours, microencapsulation was completed. After collecting the thus formed microcapsules by filtration and washing thereof with water, the thus washed microcapsules were dried in a hot-air drier at 35° C. to obtain the powdery microcapsules of 5 to 20 micrometers in diameter.

Preparation of an Adhesive Agent of Microcapsule Type

Into a solution of 100 parts by weight of masticated neoprene rubber in 500 parts by weight of toluene, 1 part by weight of a phenol resin and 1 part by weight of a coumarone resin were dissolved, and into the thus obtained solution (referred to as vehicle in Example 17), 20 parts by weight of the powdery microcapsules were uniformly mixed to prepare an adhesive agent of microcapsule type.

COMPARATIVE EXAMPLE 3

Preparation of an Adhesive Agent of Microcapsule Type Without Using any Polyvalent Isocyanate In the same procedures as in Example 15 except for not using any polyvalent isocyanate, namely, Coronat ® L, an adhesive agent of microcapsule type was prepared.

TEST EXAMPLE 1

Test on the Adhesive Agents Prepared Respectively in Example 15 and Comparative Example 3

The adhesive agent of microcapsule type prepared in Example 15 was painted on a sheet of polyvinyl chloride of 0.5 mm in thickness at a rate of 6 g/m², and after drying the painted sheet for 2 hours at 40° C., it was found that the painted surface of the sheet showed no adhesiveness to any thing.

Onto the thus painted surface of the sheet, another sheet of polyvinyl chloride of the same dimensions was piled, the thus piled pair of sheets was passed between a pair of pinch rolls adjusted to show a rolling pressure of 10 kg/cm².

The same piled pair of sheets prepared by the same procedures as above was passed between a pair of pinch rolls adjusted to show a rolling pressure of 200 kg/cm².

As a result of examining the adhesiveness of the two pairs of piled sheets prepared as above and kept in a room for 24 hours as they were, the two sheets of every pair of sheets adhered firmly together not to be individually moved or separated to each other by hands.

On the other hand, of the two pairs of sheets prepared by the same procedures as above except for using the adhesive agent prepared in Comparative Example 3, the one prepared by passing through the pair of pinch rolls showing a rolling pressure of 10 kg/cm² showed a very poor adherence between the two sheets, and the other pair passed between the pair of rolls with a rolling pressure of 200 kg/cm² showed a considerable adhesion between the two sheets.

EXAMPLE 16

Preparation and Test of an Adhesive Agent of Solution Type

Into an aqueous mixture consisting of 10 g of a water-soluble cationic urea resin (Uramin ® P-1500, made by Mitsui-Toatsu Co., Ltd.), 150 g of water, 5 g of aqueous 10% solution of triethanolamine, 4 g of aqueous 6% solution of citric acid and 1.0 g of aqueous 10% solution of Neoperex ® (refer to Example 15), 75 ml of a 5% xylenic solution of butyl perbenzoate containing 8 g of Coronate ® L (refer to Example 15) dissolved therein was dispersed as minute droplets of 20 to 50 micrometers in diameter. After adding both 40 g of M4F prepolymer and 30 g of U 1.8 F prepolymer into the thus prepared aqueous dispersion while gently stirring the aqueous dispersion, it was adjusted to pH of 3.8 by the addition of aqueous 10% solution of citric acid. After reacting the thus treated aqueous dispersion for 5 hours, the reaction mixture was adjusted to pH of 3.0 by the addition of aqueous 20% solution of citric acid, and the reaction was continued for further 20 hours to finish microcapsulation.

Separately, into a mixed solvent of 150 parts by weight of butyl acetate, 120 parts by weight of ethyl acetate and 30 parts by weight of methyl isobutyl ketone, 7 parts by weight of polymethyl methacrylate were dissolved, and after adding 40 parts by weight of methyl methacrylate and 1.0 part by weight of N,N-dimethyl-p-toluidine to the thus formed solution, 6.5 parts by weight of the above-mentioned microcapsules were mixed with the mixture to obtain an adhesive agent of solution type.

After painting the thus prepared adhesive agent of solution type onto one side of a mild steel plate by spraying, and drying the thus sprayed adhesive agent, another mild steel plate was piled on the thus painted surface of the first mild steel plate and by applying a pressure of 10 kg/cm² onto the thus piled steel plate, the microcapsules on the painted membrane were broken. A strong adhesion was found between the thus piled two plates after a few minutes.

COMPARATIVE EXAMPLE 4

Preparation and Test of an Adhesive Agent of Solution Type Prepared Without Using Any Polyvalent Isocyanate In the same procedures as in Example 16 except for not adding Coronate ® L into the 5% xylenic solution of butyl perbenzoate, microcapsules were produced.

After preparing an adhesive agent of solution type by the same procedures as in Example 16, it was applied to the same kind of mild steel plate as in Example 16 to obtain a pair of steel plates piled together. However, on applying a pressure of 10 kg/cm² to the thus piled pair of steel plates, no favorable adhesion was obtained between the two plates.

TEST EXAMPLE 2

Application of the Adhesive Agent of the Present Invention

On the peripheral part of a sheet of paper which is to be folded and is made to be an envelope, the adhesive agent prepared in Example 16 was painted at a width of 3 mm by a flexo-printing method. The thus prepared sheet of paper for an envelope did not stick when it was preserved or used for writing thereon, and after writing a series of necessary items thereon and then folding, the folded sheet was passed between a pair of pinch rolls at a rolling pressure of 300 kg/cm², thereby a completely sealed envelope was obtained.

EXAMPLE 17

Preparation and Application of an Adhesive Agent

Into an aqueous mixture of 3 g of Uramin® P-1500 (refer to Example 16), 30 ml of water, 1.5 g of aqueous 10% solution of triethanolamine, 1.0 g of aqueous 10% solution of citric acid and 0.45 g of aqueous 6% solution of Neoperex® (refer to Example 15), 15 ml of xylenic solution containing 0.2 g of triisocyanatotriphenylmethane dissolved therein were dispersed as minute droplets of 10 to 30 micrometers in diameter. Into the thus prepared dispersion, both 12 g of M6F prepolymer and 6 g of U 1.8 F prepolymer were added, and after adjusting the pH of the mixture to 3.6 by the addition of aqueous 10% solution of citric acid, the mixture was reacted for one hour under a gentle stirring.

Then, 30 ml of water were added to the reaction system, the reaction was still continued for 4 hours, and after reducing the pH of the reaction system to 3.0 by the addition of aqueous 20% solution of citric acid, the system was still reacted for 15 hours to complete the microencapsulation of xylene.

The thus prepared microcapsules were collected and treated as in Example 15 to obtain powdery microcapsules.

The thus obtained powdery microcapsules were applied to prepare the envelopes of heat-sensitive paper as follows.

On the peripheral part of a continuous sheet of heat-sensitive paper which was provided with successive, minute holes for folding or opening and made to be envelopes by bending in S-mode, an adhesive agent of microcapsule type prepared by dispersing the powdery microcapsules in the same vehicle as that used in Example 15 was painted at a width of 4 mm by flexo-printing method.

After printing a series of necessary information on the thus partially painted sheet of heat-sensitive paper in a computer, the sheet was cut into individual pieces and the thus cut pieces were passed between a pair of pinch rolls of a rolling pressure of 250 kg/cm² to obtain the individual completely sealed envelopes made of the sheet of heat-sensitive paper. In the time of printing in the computer, the sheet of heat-sensitive paper thus partially painted with the adhesive agent did not stick even when a separating paper was not used.

What is claimed is:

1. A microcapsule containing a hydrophobic, volatile substance as the core substance, wherein a wall membrane of the microcapsule comprises a polymeric material formed by the interfacial polymerization of a polyvalent isocyanate which is at least one member selected from the group consisting of tolylene diisocyanates, diisocyanate diphenylmethanes, hexamethylene diisocyanates, polymethylene polyphenyl isocyanates, triisocyanatotriphenylmethanes, dimers of tolylene diisocyanates and trimers of tolylene diisocyanates, with a water-soluble cationic urea resin and a prepolymer of an aminoresin, and a polymeric material formed by the polycondensation of the water-soluble cationic urea resin with the prepolymer of an aminoresin in the presence of a low-molecular anionic surfactant.

2. The microcapsule of claim 1, wherein the hydrophobic, volatile substance is a hydrophobic, organic compound showing a vapor pressure of higher Than 30 mmHg at 100° C.

3. The microcapsule of claim 1, wherein the prepolymer of aminoresin is at least one prepolymer selected from the group consisting of prepolymers of melamine-formaldehyde, prepolymers of urea-formaldehyde, prepolymers of melamine-urea-formaldehyde, prepolymers of melamine-thiourea-formaldehyde and prepolymers of melamine-thiourea-urea formaldehyde, or a mixed prepolymer containing a prepolymer of melamine-formaldehyde and a prepolymer of thiourea-formaldehyde.

4. A process for producing a microcapsule containing a hydrophobic, volatile substance as the core substance, comprising dispersing the said hydrophobic, volatile substance containing a polyvalent isocyanate which is at least one member selected from the group consiting of tolylene diisocyanates, diisocyanate diphenylmethanes, hexamethylene diisocyanates, polymethylene polyphenyl isocyanates, triisocyanatotriphenylmethanes, dimers of tolylene diisocyanates and trimers of tolylene diisocyanates in an aqueous medium containing a water-soluble cationic urea resin, a low-molecular anionic surfactant and at least one prepolymer of aminoresin, and maintaining the pH of the resultant dispersion within an acidic range by adding an acid catalyst to interfacially polymerize the polyvalent isocyanate with the water-soluble cationic urea resin and the at least one prepolymer and to precondense the water-soluble cationic urea resin with at least one prepolymer.

5. The process of claim 4 comprising using as the hydrophobic, volatile substance a hydrophobic, organic compound having a vapor pressure higher than 30 mmHg at 100° C.

6. The process of 13, comprising using 0.1 to 50 parts by weight of the polyvalent isocyanate contained in 100 parts by weight of the hydrophobic, volatile substance.

7. The process of claim 4, comprising using as the prepolymer of aminoresin at least one prepolymer selected from the group consisting of prepolymers of melamine-formaldehyde, prepolymers of urea-formaldehyde, prepolymers of melamine-ureA-formaldehyde, prepolymers of melamine-thiourea-formaldehyde and prepolymers of melamine-thiourea-urea-formaldehyde or a mixed prepolymer containing a prepolymer of melamine-formaldehyde and a prepolymer of thiourea-formaldehyde.

* * * * *